United States Patent [19]

Matsubara et al.

[11] Patent Number: 5,112,841
[45] Date of Patent: May 12, 1992

[54] IMIDAZOLE DERIVATIVES AND ANTIEPILEPTICS COMPRISING SAID IMIDAZOLE DERIVATIVES AS EFFECTIVE INGREDIENTS

[75] Inventors: Akira Matsubara, Yokohama; Kazuya Sakai, Mobara; Hideki Tanada, Mobara; Akira Mizuchi, Mobara; Kazutoshi Horikomi, Mobara; Takuma Ohtsu, Mobara, all of Japan

[73] Assignee: Mitsui Toatsu Chemicals, Incorporated, Tokyo, Japan

[21] Appl. No.: 661,981

[22] Filed: Feb. 28, 1991

[30] Foreign Application Priority Data

Mar. 6, 1990 [JP] Japan .................... 2-52799

[51] Int. Cl.⁵ .................. C07D 417/14; C07D 413/14; A61K 31/42; A61K 31/425
[52] U.S. Cl. .................... 514/361; 514/364; 514/367; 514/370; 514/372; 514/375; 514/377; 514/380; 548/128; 548/133; 548/159; 548/181; 548/206; 548/222; 548/233; 548/245
[58] Field of Search .............. 548/159, 133, 128, 181, 548/206, 222, 233, 245; 514/361, 364, 367, 375, 370, 377, 376, 380

[56] References Cited

FOREIGN PATENT DOCUMENTS 0003901 9/1979 European Pat. Off. .
0069513 1/1983 European Pat. Off. .
0298921 1/1989 European Pat. Off. .
2045244 10/1980 United Kingdom .

OTHER PUBLICATIONS

Chemical Abstracts, vol. 101, No. 19, Nov. 5, 1984, V. Cavrini et al, "Syntheses and in vitro antimycotin activities of 1-benzyl-3-[1-imidaxolylmethyl] indoles" p. 696; ref. No. 171173s.

Primary Examiner—Robert Gerstl
Attorney, Agent, or Firm—Nixon & Vanderhye

[57] ABSTRACT

Described herein are imidazole derivatives having a specific structure and satisfactory as antiepileptics from the standpoint of the strength of action, prolonged action and side effects as well as their preparation processes.

2 Claims, No Drawings

IMIDAZOLE DERIVATIVES AND ANTIEPILEPTICS COMPRISING SAID IMIDAZOLE DERIVATIVES AS EFFECTIVE INGREDIENTS

BACKGROUND OF THE INVENTION

1. Field of the Invention

This invention relates to imidazole derivatives and physiologically acceptable salts thereof, said derivatives and salts having antiepileptic action, and antiepileptics containing the derivatives and salts as effective ingredients. The imidazole derivatives of the present invention are useful for the treatment of convulsive diseases such as epilepsy

2. Description of the Related Art

Some imidazole derivatives having antiepileptic action have been known to date. Reference may be had, for example, to Japanese Patent Laid-Open Nos. 81269/1979, 19294/1980 and 29376/1989.

Furthermore, phenobarbital, phenytoin and sodium valproate are widely used as antiepileptics for the treatment of convulsive diseases such as epilepsy.

They are however not fully satisfactory in the strength of action, prolonged action and the level of side effects.

SUMMARY OF THE INVENTION

An object of the present invention is to provide an imidazole derivative useful as an effective ingredient in an antiepileptic which is satisfactory in overall aspects, including the strength of action, prolonged action and side effects.

Another object of the present invention is to provide an antiepileptic comprising the imidazole derivative or a physiologically acceptable salt thereof as an effective ingredient.

In one aspect of the present invention, there is thus provided an imidazole derivative represented by the following formula (I):

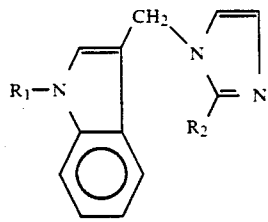

wherein $R_1$ means

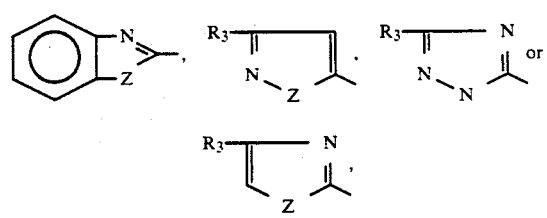

$R_3$ being a phenyl group optionally substituted by at least one substituent selected from the group consisting of halogen atoms and lower alkyl, lower alkoxy, trifluoromethyl and cyano groups and Z being a sulfur or oxygen atom, and $R_2$ denotes a hydrogen atom or a lower alkyl group. The lower alkyl group and the lower alkoxyl group may desirably contain 1 or 2 carbon atoms.

The imidazole derivative of this invention represented by the formula (I) and its physiologically-acceptable salts have excellent antiepileptic action and high safety and are extremely useful as effective ingredients in antiepileptics.

DETAILED DESCRIPTION OF THE INVENTION AND PREFERRED EMBODIMENTS

Exemplary, physiologically-acceptable acid additions salts of the imidazole derivative of the present invention include inorganic acid salts formed using hydrochloric acid, sulfuric acid, phosphoric acid and the like and organic acid salts formed using acetic acid, citric acid, succinic acid, maleic acid, fumaric acid, tartric acid, methanesulfonic acid, lactic acid and the like.

The imidazole derivative of the present invention can be obtained by any one of processes containing the following preparation routes and processes to be described in the subsequent examples.

General synthetic routes:

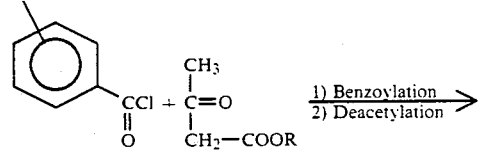

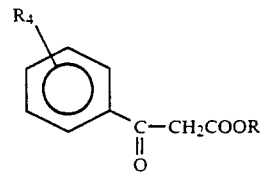

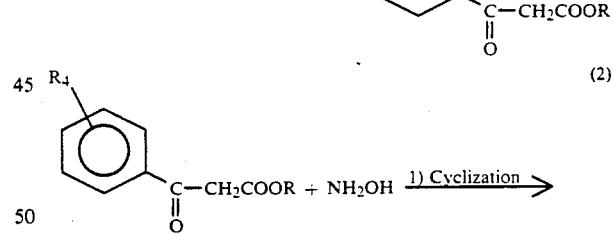

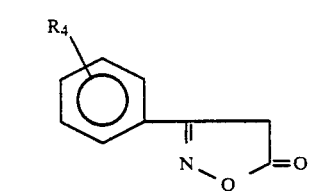

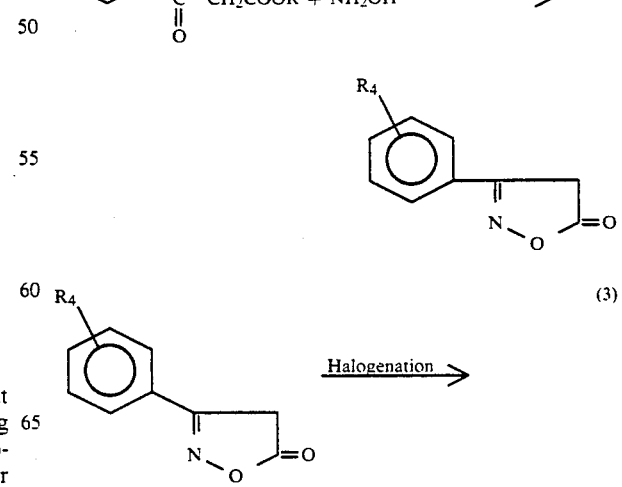

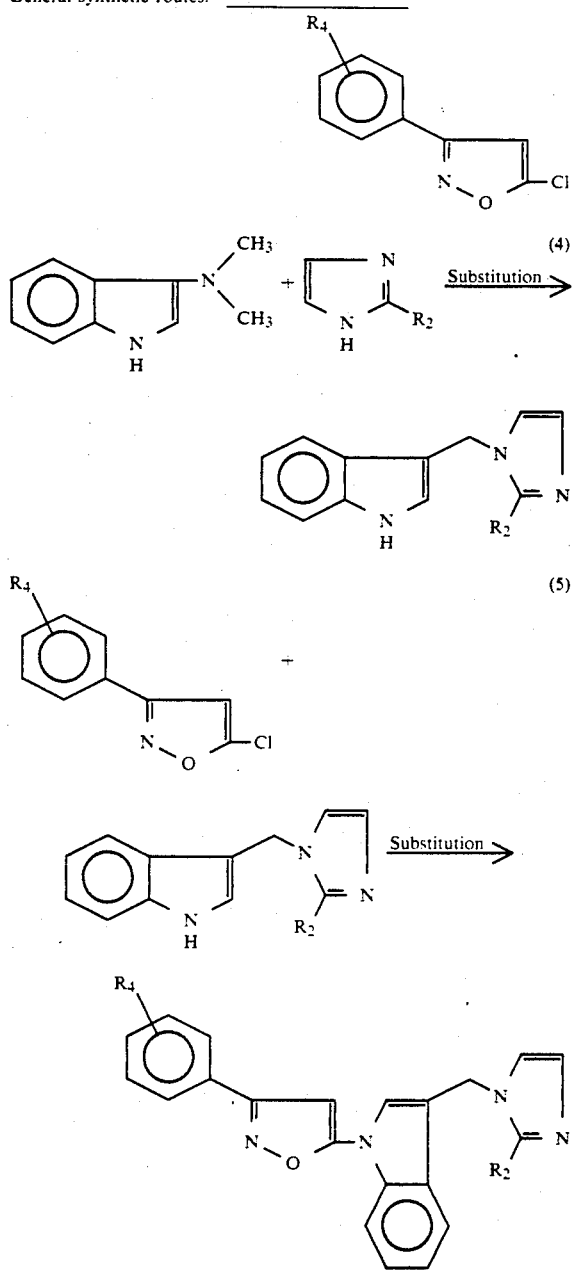

General synthetic routes:
-continued

In the above reaction formulae, $R_4$ means a halogen atom or a lower alkyl, lower alkoxyl, trifluoromethyl or cyano group, $R_2$ denotes a hydrogen atom or a lower alkyl group similar to that represented by the general formula (I). R stands for an ester residual group.

Although the dosage of the imidazole derivatives according to this invention to a patient varies depending on the conditions to be treated and the manner of administration, its daily dosage may generally be 5–1,000 mg, preferably 50–300 mg per adult.

The imidazole derivatives can be formulated into a dosage form such as an oral dosage form, e.g., capsules, tablets, a fine granule, a syrup or a powder, an injection or suppositories and can be administered orally or parenterally.

As additives for the formulation into dosage forms, excipients (lactose, corn starch, sugar, sorbit, calcium phosphate, etc.), binders (syrup, arabic gum, gelatin, sorbit, polyvinylpyrrolidone, hydroxypropyl-cellulose, etc.), lubricants (magnesium stearate, talc, polyethylene glycol, silica, etc.), disintegrators (potato starch, carboxymethylcellulose, etc.), wetting agents (sodium laurylsulfate, etc.), etc. are used as needed depending on the dosage form.

(Effects of the Invention)

Antiepileptic action of certain imidazole derivatives of this invention was verified by the following animal experiments.

Experiment 1: Maximal Electroshock Seizure Test ddy Male mice (body weight: 25–30 g) were used in groups each of which consisted of 5–10 mice. A test compound was orally administered. One hour later, an electric shock (200 Hz, 50 mA, 0.2 second) was applied through corneal electrodes. The mice were observed for tonic-extensor convulsions of hind legs. Antiepileptic action (%) was calculated in accordance with the following calculation formula, and $ED_{50}$ (mg/Kg) was determined therefrom.

Antiepileptic action (%) =

$$\frac{\text{Number of mice not developed the tonic component}}{\text{Number of mice used}} \times 100$$

TABLE 1

| Example No. | $ED_{50}$(mg/Kg) |
|---|---|
| 1 | 9 |
| 3 | 20–40 |
| 4 | 20–40 |
| 5 | 16 |
| 6 | 7 |
| 7 | 20–40 |
| 8 | 20–40 |
| 9 | 20–40 |
| 10 | 20–40 |
| 11 | 14 |
| Phenytoin.Na | 7 |

Experiment 2: Rotorod Test ddy Male mice (body weight: 25–30 g) were used in groups each of which consisted of 5–10 mice. A test compound was orally administered One hour later, each mouse was placed on a rod which rotated a full turn per second. Mice which fell down within 120 seconds were counted. Rotorod action (%) was calculated in accordance with the following calculation formula, and $ED_{50}$ (mg/Kg) was determined therefrom.

Rotorrod action (%) =

$$\frac{\text{Number of mice fell down within 120 sec.}}{\text{Number of mice used}} \times 100$$

The results are summarized in table 2.

TABLE 2

| Example No. | $ED_{50}$(mg/Kg) |
|---|---|
| 1 | 500 |
| 6 | >750 |
| 11 | >750 |
| Phenytoin.Na | 186 |

Experiment 3: Traction Test ddy Male mice (body weight: 25-30 g) were used in groups each of which consisted of 5-10 mice. A test compound was orally administered. One hour later, each mouse was caused to hold with the fore paws thereof a stainless steel wire whose diameter was 1.5 mm. Mice which failed to hold the wire with the hind legs in 5 seconds or which fell down from the wire in the same period were counted. Traction activity (%) was calculated in accordance with the following calculation formula, and $ED_{50}$ (mg/Kg) was determined therefrom.

$$\text{Traction activity (\%)} = \frac{\text{Number of mice failed to hold the wire with the hind legs in 5 seconds or which fell down from the wire in the same period}}{\text{Number of mice used}} \times 100$$

The results are summarized in Table 3.

TABLE 3

| Example No. | $ED_{50}$(mg/Kg) |
|---|---|
| 1 | >750 |
| 6 | >750 |
| 11 | >750 |
| Phenytoin.Na | 350 |

Experiment 4: Acute Toxicity ddy Male mice (body weight: 25-30 g) were used in groups each of which consisted of 5-6 mice. A test compound was orally administered. Mice which died in 5 days were counted. Death rate (%) wa calculated in accordance with the following calculation formula, and $LD_{50}$ (mg/Kg) was determined therefrom.

$$\text{Death rate (\%)} = \frac{\text{Number of mice died in 5 days}}{\text{Number of mice used}} \times 100$$

The results are shown in Table 4.

TABLE 4

| Example No. | $ED_{50}$(mg/Kg) |
|---|---|
| 1 | >1000 |
| 6 | >1000 |
| 11 | >1000 |
| Phenytoin.Na | 300-500 |

The present invention will hereinafter be described in detail by the following referential examples and examples.

Referential Example 1

3-Phenyl-5-chloroisoxazole (1) 3-Phenyl-5-isoxazolone

In accordance with the known process [Canadian Journal of Chemistry, 4s, 1371 (1970)], 154 g (0.8 mol) of ethyl benzoylacetoacetate were dissolved in 1 l of acetic acid, and 55.7 g (0.8 mol) of hydroxylamine hydrochloride were then added to the resulting solution, followed by heating under stirring at 100° C. for 5 hours. After the solvent was distilled off, ethyl alcohol was added to the residue to precipitate crystals. The crystals were collected and then washed with ethyl alcohol, whereby the title compound was obtained as colorless crystals.

Yield: 72 g (56%).

Melting point: 149°-151° C.

(2) 3-Phenyl-5-chloroisoxazole

To 84.3 g (0.55 mol) of phosphorus oxychloride, 18.3 g (0.11 mol) of 3-phenyl-5-isoxazolone were added under stirring. While the internal temperature was maintained at 0°-10.C., 11.1 g (0.11 mol) of triethylamine were added further. They were then reacted under heating and stirring at 100°-120° C. for 3 hours. The reaction mixture was allowed to stand overnight at room temperature, and precipitated insoluble matter was filtered off. After the filtrate thus obtained was concentrated under reduced pressure, the residue was transferred into 500 ml of ice water, followed by neutralization with sodium hydrogencarbonate. The solution was extracted with ethyl ether. The organic layer was washed with water and then dried. The solvent was distilled off and the residue was purified by silica gel column chromatography (solvent: hexane/ethyl acetate=20/1), whereby the title compound was obtained as colorless crystals.

Yield: 15.4 g (76%)

Melting point: 47°-49° C.

Other 3-(substituted phenyl)-5-chloroisoxazole derivatives were also synthesized from the corresponding 3-(substituted phenyl)-5-isoxazolone in a similar manner to Referential Example 1.

Referential Example 2

2-Chloro-4-phenylthiazole

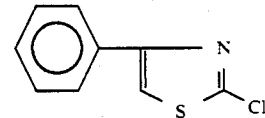

(1) α-Thiocyanoacetophenone

In accordance with the known process (Beilstein, 8, 94), 10.0 g (50 mmol) of o-bromoacetophenone and 4.9 g (50 mmol) of potassium thiocyanate were added to 80 ml of ethyl alcohol, and the resultant mixture was heated at 80° C. for 3 hours and then allowed to stand overnight. Added to the reaction mixture were 50 ml of water. Precipitated crystals were collected by filtration, washed with 50% aqueous ethyl alcohol and then dried, whereby the title compound was obtained as colorless crystals.

Yield: 8.7 g (98%).

Melting point: 75°-77° C. (literature value: 74° C.).

(2) 2-Hydroxy-4-phenylthiazole

Following the known process [Bull. Soc. Chem. France, 11, 2498 (1963)], 8.85 g (50 mmol) of α-thiocyanoacetophenone, 5 ml of water and 1.3 ml of concentrated sulfuric acid were added to 40 ml of acetic acid and the resultant mixture was refluxed for 2 hours. The reaction mixture was then allowed to stand overnight at room temperature. Precipitated crystals were collected by filtration and then washed with water, whereby the title compound was obtained a colorless crystals.

Yield: 7.7 g (87%).

Melting point: 205°-206° C. (literature value: 208°-210° C.).

(3) 2-Chloro-4-phenylthiazole

To 80 ml of phosphorus oxychloride were added 7.7 g (43 mmol) of 2-hydroxy-4-phenylthiazole, followed by heating at 100°–105° C. for 2 hours. The solvent was then distilled off from the reaction mixture under reduced pressure. Ice water was added to the residue, followed by extraction with ethyl ether. The ether layer was washed with water. After purification by silica gel column chromatography (solvent: hexane/ethyl acetate=5/1), the title compound was obtained as pale yellow crystals.

Yield: 6.3 g (74%).
Melting point: 57°–59° C.

Referential Example 3

3-Phenyl-5-chloro-1,2,4-oxadiazole

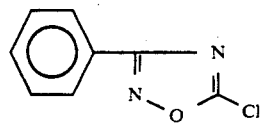

(1) o-Ethoxycarbonylbenzamidoxime

Following the known process [Ber, 18, 2467 (1875)], a solution of 13.4 ml (0.14 mol) of ethyl chlorocarbonate in 100 ml of chloroform was added dropwise to a solution of 38.2 g (0.28 mol) of benzamidoxime hydrochloride in 380 ml of chloroform. After completion of the dropwise addition, the reaction mixture was stirred at room temperature for 3 hours. The benzamidoxime thus precipitated was filtered off and the filtrate was concentrated under reduced pressure. The residue was dissolved in 100 ml of ethyl alcohol, to which 30 ml, of water were added. Most ethyl alcohol was then distilled off under reduced pressure. Crystals thus formed were collected by filtration, washed with water and then dried under reduced pressure, whereby the title compound was obtained as colorless crystals.

Yield: 27.0 g (91%).
Melting point: 126°–128° C. (literature value: 127° C.).

(3) 3-Phenyl-1,2,4-oxadiazol-5-ol

In accordance with the known process [Yakugaku Zasshi, 84(11), 1061 (1964)], 27 g (0.13 mol) of o-ethoxycarbonylbenzamidoxime were added to a liquid mixture consisting of 10 g (0.25 mol) of sodium hydroxide, 600 ml of water and 150 ml of ethyl alcohol, followed by stirring at room temperature for 3 hours. The reaction mixture was neutralized with dilute hydrochloric acid. Crystals thus formed were collected by filtration and then washed with water, whereby the title compound was obtained as colorless crystals.

Yield: 12.6 g (60%).
Melting point: 200°–202° C. (literature value: 203°–204° C.).

(3) 3-Phenyl-5-chloro-1,2,4-oxadiazole

To 53 g of phosphorus oxychloride were added 12.6 g (18 mmol) of 3-phenyl-1,2,4-oxadiazol-5-ol, followed by the further addition of 2.8 g (35 mmol of pyridine. The resultant mixture was heated under stirring for 8 hours. The reaction mixture was allowed to cool down to room temperature and then transferred into 500 ml of ice water. The resultant liquid mixture was extracted with ether. The extract was washed successively with water, a 5% aqueous solution of sodium hydroxide and water. The organic layer was dried and the solvent was distilled off. When the residue was left over under cooling, the title compound was obtained as pale brown crystals.

Yield: 10 g (71%).
Melting point: 40°–42° C.

Referential Example 4

3-(4-Methoxyphenyl)-5-chloroisoxazole

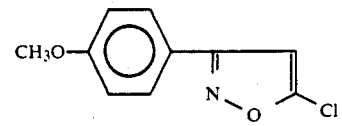

(1) Ethyl 4-methoxybenzoylacetate

To a liquid mixture consisting of 25 ml of solvent naphtha and 50 ml of water, 19.5 g (0.15 mol) of ethyl acetoacetate were added, followed by cooling to 5° C. A 33% aqueous sodium hydroxide solution (6.5 ml) was added to the resultant liquid mixture, followed by vigorous agitation. A 33% aqueous sodium hydroxide solution (27 ml) and 27.6 g (0.16 mol) of 4-methoxybenzoyl chloride were simultaneously added in small portions over 30 minutes, whereby they were reacted while the internal temperature and pH were maintained below about 10° C. and at about 11, respectively. After completion of the dropwise addition, the reaction mixture was stirred at room temperature for 2.5 hours to allow the reaction to proceed further. After completion of the reaction, 8 g (0.15 mol) of $NH_4Cl$ were added further and the resulting mixture was allowed to stand overnight. An oil thus formed was extracted with ethyl acetate. The organic layer was washed with water and then dried. The solvent was distilled off and the residue was purified by silica gel column chromatography (solvent: hexane/ethyl acetate=5/1), whereby the title compound was obtained as a colorless oil. Yield: 16.1 g (48%)

NMR($\delta$ ppm, $CDCl_3$): 1.26(3H,t,J=6Hz)
3.84(3H,s)
3.92(2H,s)
4.18(2H,q,J=6Hz)
6.92(2H,d,J=8Hz)
7.92(2H,d,J=8Hz).

(2) 3-(4-Methoxyphenyl)-isoxazol-5-one

To 110 ml of acetic acid were added 16 g (72 mmol) of ethyl 4-methoxybenzoylacetate and 5 g (72 mmol) of hydroxyamine hydrochloride, followed by stirring at 100° C. for 2 hours. The resulting mixture was allowed to stand overnight at room temperature. The reaction mixture was concentrated under reduced pressure. Crystals thus precipitated were collected by filtration, washed with water and then dried under reduced pressure, whereby the title compound was obtained as pale yellow crystals.

Yield: 5.8 g (42%).
Melting point: 144°–146° C.

NMR($\delta$ ppm, $DMSO-d_6$): 3.84(3H,s) 4.26(1H,s) 5.60(1H,s) 7.06(2H,d,J=8Hz) 7.70 (2H,d,J=8Hz).

3) 3-(4-Methoxyphenyl)-5-chloroisoxazole

To 30 g of phosphorus oxychloride were added 7.4 g (39 mmol) of 3-(4-methoxyphenyl)isoxazol-5-one, followed by the dropwise addition of 4 g (40 mmol) of triethylamine. After completion of the dropwise addition, the reaction mixture was stirred at 120°–125° C. for 4 hours. The solvent was then distilled off under reduced pressure. Ice water (100 ml) was added to the residue, and the resulting mixture was extracted with ethyl acetate. The organic layer was washed with water and then dried. Purification by silica gel column chromatography (solvent: hexane/ethyl acetate=10/1) gave the title compound as colorless crystals.

Yield: 2.8 g (35%)
Melting point: 82°-83° C.
NMR(δ ppm, CDCl₃): 3.86(3H,s)
6.40(1H,s)
6.96(2H,d,J=8Hz)
7.68(2H,d,J=8Hz).

Referential Example 5

3-(1-Imidazolyl)methylindole

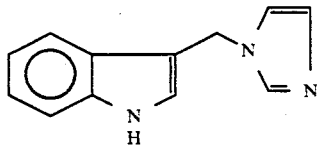

To 10 ml of xylene were added 0.87 g (5 mmol) of gramine and 0.68 g (10 mmol) of imidazole, followed by refluxing for 2 hours. The solvent was distilled off under reduced pressure from the reaction mixture and the residue was extracted with ethyl acetate. After the extract was washed with water, the organic layer was dried and then concentrated so that 3-(1-imidazolyl)methylindole, the title compound, was obtained as colorless crystals.

Yield: 0.81 g (83%)
Melting point: 177°-179° C.
NMR(δ ppm, CDCl₃): 5.30(2H,s)
6.96(1H,s)
7.05(1H,s)
7.09-7.26(3H,m)
7.35-7.45(2H,m)
7.58(1H,s)
8.67(1H,br).

Referential Example 6

3-{1-(2-methylimidazolyl)]methylindole

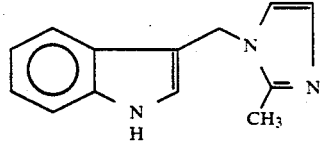

To 40 ml of xylene were added 3.48 g (20 mmol) of gramine and 3.3 g (40 mmol) of 2-methylimidazole, followed by refluxing for 2 hours. The reaction mixture was then processed in a similar manner to Referential Example 5, whereby 3-(1-(2-methylimidazolyl)]methylindole, the title compound, was obtained as colorless crystals.

Yield: 3.3 g (78%).
Melting point: 173°-174.5° C.
NMR(δ ppm, DMSO-d₆): 2.34(3H,s)
5.22(2H,s)
6.44(1H,s)
6.8-7.2(2H,m)
7.2-7.5(2H,m)
11.1(1H,bs).

Example 1

1-(3-Phenyl-5-rsoxazolyl)-3-(1-imidazolyl)methylindole hydrochloride

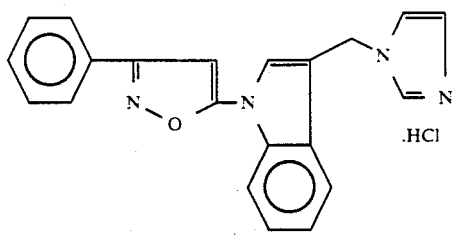

To 15 ml of dry DMF was added 0.16 g (4 mmol) of 60% sodium hydride, to which 0.8 g (4 mmol) of 3-(1-imidazolyl)methylindole synthesized by the process of Referential Example 5 was added under stirring. The resultant mixture was stirred at room temperature for 30 minutes. Added next to the reaction mixture was 0.73 g (4 mmol) of 3-phenyl-5-chloroisoxazole, followed by stirring at room temperature for 5 hours. The solvent was distilled off under reduced pressure. Water was added to the residue, followed by extraction with ethyl acetate. The extract was washed with water, dried and then concentrated. The concentrate was purified by silica gel column chromatography (solvent: chloroform/methyl alcohol =50/1), whereby 1-(3-phenyl-5-isoxazolyl)-3-(1-imidazolyl)methylindole hydrochloride, the title compound, was obtained as colorless crystals.

Yield: 0.8 g (59%)
Melting point: 133°-134° C.
NMR(δ ppm, CDCl₃): 5.12(2H,s)
6.38(1H,s)
6.80-7.90(13H,m).

(2) 1-(3-Phenyl-5-isoxazolyl-3-(1-imidazolyl)methylindole hydrochloride

In 10 ml of dioxane was dissolved 0 8 g (2.4 mmol) of I-(3-phenyl-5-isoxazolyl)-3-(1-imidazolyl)-methylindole. After a 4 N dioxane hydrochloride solution was added in the amount of 5 ml under ice cooling, excess 4 N dioxane hydrochloride solution as the reaction solvent was distilled off. Ethyl acetate was added to the residue and crystals thus formed were collected by filtration, whereby the title compound was obtained as colorless crystals.

Yield: 0.46 g (52%).
Melting point: 213°-215° C.
Elemental analysis:
Calculated for C₂₁H₁₆N₄O.HCl: C: 66.93, H: 4.55, N: 14.87, Cl: 9.41. Found: C: 66.21, H: 4.47 N: 14.59, Cl: 9.08.

EXAMPLE 2

1-(3-Phenyl-5-isoxazolyl)-3-(1-(2-methyl-imidazolyl))methylindole hydrochloride

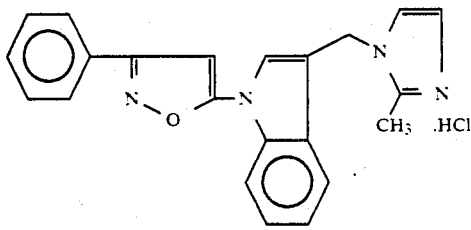

To 30 ml of dry DMF was added 0.4 g (10 mmol) of 60% sodium hydride, to which 2.11 g (10 mmol) of 3-{1-(2-methylimidazolyl)}methylindole synthesized by the process of Referential Example 6 was added under ice cooling. The resultant mixture was stirred at room temperature for 30 minutes. Added next to the reaction mixture was 1.79 g (10 mmol) of 3-phenyl-5-chloro-isoxazole, followed by stirring at room temperature for 5 hours. After the solvent was distilled off, water was added and the reaction product was extracted with ethyl acetate. The extract was washed with water. The organic layer was dried over magnesium sulfate and then concentrated. The residue was recrystallized from a mixed solvent of hexane and ethyl acetate, whereby the title compound was obtained as colorless crystals.

Yield: 1.4 g (40%).
Melting point: 114°–116° C.
NMR(δ ppm, DMSO-$d_6$): 2.43(3H,s)
5.38(2H,s)
6.82(1H,s)
7.2–8.2(12H.m)

By a similar procedure to Example 1(2), the above compound was converted to its hydrochloride.

EXAMPLE 3

1-{3-(4-Fluorophenyl)-5-isoxazolyl)-3-(1-imidazolyl)-methylindole hydrochloride

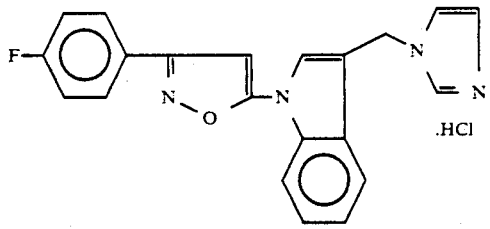

In 15 ml of dry DMF were dissolved 1.5 g (7.6 mmol) of 3-(2-imidazolyl)methylindole, followed by the addition of 0.37 g (9.3 mmol) of 60% sodium hydride under ice cooling. After the resultant mixture was stirred for 10 minutes at room temperature, 1.81 g (9.2 mmol) of 3-(4-fluorophenyl)-5-chloroisoxazole (synthesized in a similar manner to the procedures of Referential Example 1) were added. The resulting mixture was then stirred for 1.5 hours for reaction. The reaction mixture was transferred into 100 ml of ice water, followed by extraction with ethyl acetate. The organic layer was washed with water and then dried. The solvent was distilled off from the organic layer. The residue was then recrystallized from a mixed solvent of ethanol, ethyl acetate and hexane, whereby the title compound was obtained as colorless crystals. Yield: 1.6 g (58%)

Melting point: 176°–178° C.
NMR(δ ppm, CDCl$_3$): 5.36(2H,s)
6.39(1H,s)
7.01(1H.s)
7.11(1H,s)
7.17–7.32(3H,m)
7.42–7.47(3H,m)
7.65(1H,bs)
7.83–7.91(3H),m).

By a similar procedure to Example 1(2), the above compound was converted to its hydrochloride.

EXAMPLE 4

1-{3-(4-Chlorophenyl)-5-isoxazolyl }-3-(1-imidazolyl)methylindole hydrochloride

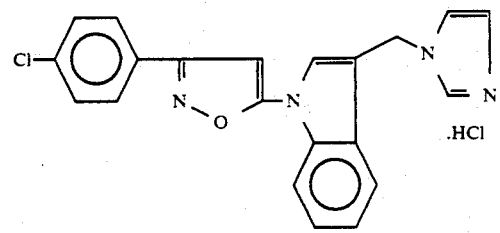

In 15 ml of dry DMF were dissolved 1.5 g (7.6 mmol) of 3-(1-imidazolyl)methylindole, followed by the addition of 0.38 g (9.5 mmol) of 60% sodium hydride under ice cooling. After the resultant mixture was stirred for 10 minutes at room temperature, 2.0 g (9.3 mmol) of 3-(4-chlorophenyl)-5-chloroisoxazole were added. The resulting mixture was then stirred for 1.5 hours at room temperature for reaction. The reaction mixture was transferred into 100 ml of ice water. Crude crystals thus formed were collected by filtration, washed with water and then dried under reduced pressure. They were recrystallized from ethyl acetate, whereby the title compound was obtained as colorless crystals.

Yield: 2.5 g (87%)
Melting point: 220°–222° C. (decomposed).
NMR(δ ppm, CDCl$_3$): 5.35(2H,s)
6.40(1H,s)
7.01(1H,s)
7.11(1H,s)
7.26–7.32(2H,m)
7.42–7.51(4H,m)
7.78(1H,s)
7.80–7.83(2H,m)
7.87–7.91(1H,bd).

By a similar procedure to Example 1(2), the above compound was converted to its hydrochloride.

EXAMPLE 5

1-(3-(p-Toluyl)-5-isoxazolyl}-3-(1-imidazolyl)-methylindole hydrochloride

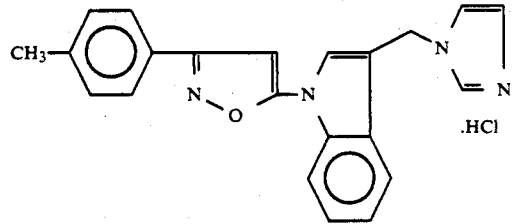

In 15 ml of dry DMF were dissolved 1.5 g (7.6 mmol) of 3-(1-imidazolyl)methylindole, followed by the addition of 0.37 g (9.3 mmol) of 60% sodium hydride under ice cooling. After the resultant mixture was stirred for 10 minutes at room temperature, 1.8 g (9.3 mmol) of 3-(p-toluyl)-5-chloroisoxazole were added. The resulting mixture was then stirred at room temperature for 7 hours. After completion of the reaction, precipitated crystals were collected by filtration and dissolved in ethyl acetate. The solution was washed with water and then dried. The solvent was distilled off and the residue was recrystallized from a mixed solvent of ethyl acetate and hexane, whereby the title compound was obtained as colorless crystals.

Yield: 1.8 g (66%)
Melting point: 207°-209° C. (decomposed).
NMR(δ ppm, CDCl₃): 2.43(3H,s)
5.35(2H,s)
6.40(1H,s)
7.01(1H,s)
7.10(1H,s)
7.28-7.33(3H,m)
7.41-7.49(3H,m)
7.65(1H,bs)
7.59(2H,d,J=8.4Hz)
7.90(1H,d,J=7.9Hz).

By a similar procedure to Example 1(2), the above compound was converted to its hydrochloride.

EXAMPLE 6

1-{3-(4-Methoxyphenyl)-5-isoxazolyl}-3-(1-imidazolyl)methylindol hydrochloride

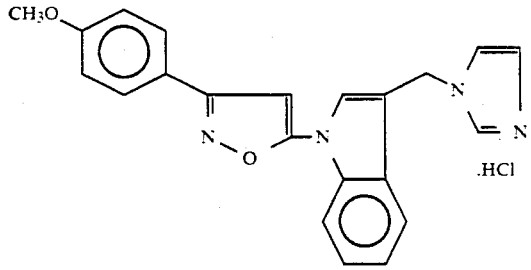

In 15 ml of dry DMF were dissolved 1.5 g (7.6 mmol) of 3-(1-imidazolyl)methylindole, followed by the addition of 0.387 g (9.53 mmol) of 60% sodium hydride under ice cooling. After the resultant mixture was stirred for 10 minutes at room temperature, 1.8 g (9.3 mmol) of 3-(p-toluyl)-5-chloroisoxazole were added. They were then reacted at room temperature for 20 minutes. Then, 1.81 g (8.6 mmol) of 3-(4-methoxyphenyl)-5-chloroisoxazole synthesized in Referential Example 4 were added to the reaction mixture and caused to react for 2.5 hours. Water was added to the reaction mixture to obtain a liquid mixture. The liquid mixture was extracted with ethyl acetate and the extract was then washed with water. After the organic layer was dried, the solvent was distilled off and ethyl acetate was added to the residue to crystallize the same, so that the title compound was obtained as colorless crystals.

Yield: 1.7 g (60%)
Melting point: 197°-198° C. (decomposed).
NMR(δ ppm, CDCl₃): 3.88(3H,s)
5.35(2H,s)
6.37(1H,s)
6.99-7.03(2H,bd)
7.10(1H,bs)
7.25-7.31(2H,m)
7.40-7.48(3H,m)
7.65(1H,s)
7.77-7.82(2H,bd)
7.90(1H,d,J=8.4Hz).

By a similar procedure to Example 1(2), the above compound was converted to its hydrochloride.

EXAMPLE 7

1-(3-(4-Cyanophenyl)-5-isoxazolyl)-3-(1-imidazolyl)methylindole hydrochloride

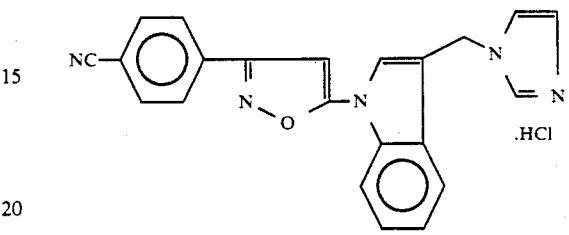

In 15 ml of dry DMF were dissolved 1.5 g (7.6 mmol) of 3-(1-imidazolyl)methylindole, followed by the addition of 0.38 g (9.5 mmol) of 60% sodium hydride under ice cooling. The resultant mixture wa stirred for 15 minutes at room temperature. To the reaction mixture, 1.72 g (8.4 mmol) of 3-(4-phenyl)-5-chloroisoxazole were then added. The resulting mixture was stirred at room temperature for 2 hours. Water was added to the reaction mixture. Precipitated crystals were collected by filtration, washed with water and then washed with ethyl acetate, whereby the title compound was obtained as colorless crystals.

Yield: 1.9 g (68%)
Melting point: 224°-225° C. (decomposed).
NMR(δ ppm, CDCl₃): 5.36(2H,s)
6.45(1H,s)
7.02(1H,s)
7.11(1H,s)
7.26-7.35(1H,m)
7.42-7.48(3H,m)
7.65(1H,s)
7.80(2H,d,J=8.4Hz)
7.89(1H,d,J=8.4Hz)
7.99(2H,d,J=7.9Hz).
IR ($\nu_{max}^{KBr}$cm$^{-1}$): 1640, 1610.

By a similar procedure to Example 1(2), the above compound was converted to its hydrochloride.

EXAMPLE 8

1-{3-(4-Trifluoromethylphenyl)-5-isoxazolyl}-3-(1-imidazolyl)methylindole hydrochloride.

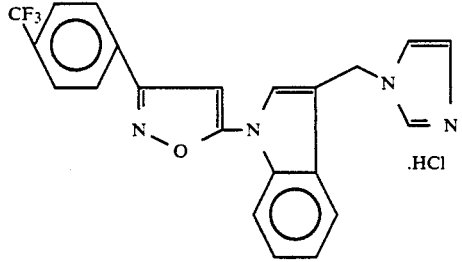

In 15 ml of dry DMF were dissolved 1.5 g (7.6 mmol) of 3-(1-imidazolyl)methylindole, followed by the addition of 0.38 g (9.5 mmol) of 60% sodium hydride under ice cooling. The resultant mixture was stirred for 15 minutes at room temperature. To the reaction mixture, 2.1 g (8.5 mmol) of 3-(4-trifluorophenyl)-5-chloroisoxazole were added further. The resulting mixture was stirred at room temperature for 2.5 hours. Water was added to the reaction mixture. Precipitated crystals were collected by filtration, washed with water and then washed with ethyl acetate, whereby the title compound was obtained as colorless crystals.

Yield: 1.9 g (61%)
Melting point: 219°-220° C.
NMR(δ ppm, CDCl$_3$): 5.36(2H,s)
6.45(1H,s)
7.01(1H,s)
7.11(1H,s)
7.27-7.39(1H,m)
7.42-7.48(3H,m)
7.65(1H,s)
7.77(2H,d,J=7.9Hz)
7.90( 1H,d,J=8.9Hz)
7.99(2H,d,J=8.4Hz).

By a similar procedure to Example 1(2), the above compound was converted to its hydrochloride.

EXAMPLE 9

1-{3-(2-Chlorophenyl)-5-isoxazolyl}-3-(1-imidazolyl)methylindole hydrochloride

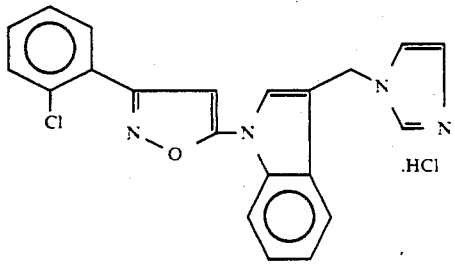

In 15 ml of dry DMF were dissolved 1.5 g (7.6 mmol) of 3-(1-imidazolyl)methylindole, followed by the addition of 0.38 g (9.5 mmol) of 60% sodium hydride under ice cooling. The resultant mixture was stirred at room temperature for 10 minutes. To the reaction mixture, a solution of 2.0 g (9.3 mmol) of 3-(2-chlorophenyl)-5-chloroisoxazole in 5 ml of dry DMF was added dropwise, followed by further reaction at room temperature for 2 hours. Water was added to the reaction mixture, followed by extraction with ethyl acetate. The organic layer was dried and then purified by silica gel column chromatography (solvent: chloroform/methyl alcohol=50/1), whereby the title compound was obtained as colorless crystals.

Yield: 2.2 g (77%)
NMR(δ ppm, CDCl$_3$): 5.35(2H,s)
6.63(1H,s)
7.00(1H,s)
7.10(1H,s)
7.25-7.31(2H,m)
7.34-7.46(5H,m)
7.65(1H,s)
7.81-7.89(2H,m).

By a similar procedure to Example 1(2), the above compound was converted to its hydrochloride. The melting point of the salt is given in Table 5.

EXAMPLE 10

1-{3-(3-Chlorophenyl)-5-isoxazolyl}-3-(1-imidazolyl)methylindole hydrochloride

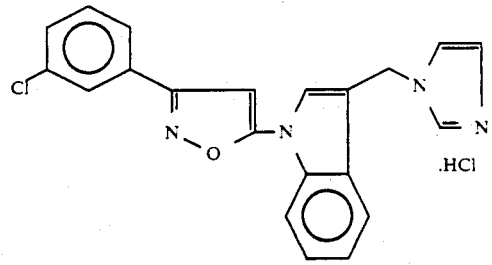

In 15 ml of dry DMF were dissolved 1.5 g (7.6 mmol) of 3-( 1-imidazolyl)methylindole, followed by the addition of 0.38 g (9.5 mmol) of 60% sodium hydride under ice cooling. The resultant mixture was stirred for 10 minutes at room temperature for reaction. After 2.0 g (9.3 mmol) of 3-(3-chlorophenyl)-5-chloroisoxazole were added, the resultant mixture was stirred at room temperature for 2 hours to react the same. Water (50 ml) was added to the reaction mixture, followed by extraction with ethyl acetate. The organic layer was washed with water, dried and then purified by silica gel column chromatography (solvent: chloroform/methyl alcohol=50/1), whereby the title compound was obtained as colorless crystals.

Yield: 1.9 g (66%)
Melting point: 143°-146° C.
NMR(δ ppm, CDCl$_3$): 5.35(2H,s)
6.39(1H,s)
7.01(1H,s)
7.09(1H,s)
7.26-7.32(2H,m)
7.41-7.50(4H,m)
7.74( 1H,s)
7.75-7.78(1H,m)
7.85-7.91(2H,m).

By a similar procedure to Example 1(2), the above compound was converted to its hydrochloride.

EXAMPLE 11

1-(3-(3-Methoxyphenyl)-5-isoxazolyl}-3-(1-imidazolyl)methylindole hydrochloride

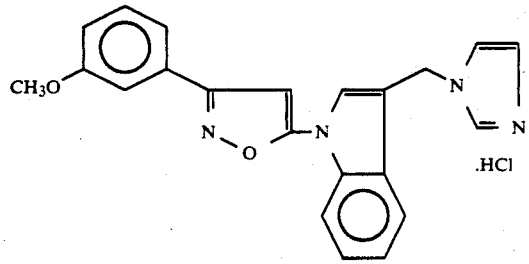

In 15 ml of dry DMF were dissolved 1.5 g (7.6 mmol) of 3-( I-imidazolyl)methylindole, followed by the addition of 0.38 g (9.5 mmol) of 60% sodium hydride under ice cooling. After the resultant mixture was stirred at room temperature for 10 minutes, were added 1.81 g (8.6 mmol) of 3-(3-methoxyphenyl)-5-chloroisoxazole synthesized in a similar manner to the procedures of Referential Example 1. They were reacted at room temperature for 3 hours under stirring. Water was added to the reaction mixture, followed by extraction with ethyl acetate. The organic layer was washed with water and then dried. The solvent was distilled off from the organic layer. The residue was then purified by silica gel column chromatography (solvent: chloroform/ methyl alcohol=100/1), whereby the title compound was obtained as colorless crystals.

Yield: 1.5 g (53%)
Melting point: 127°–129° C.
NMR($\delta$ ppm, CDCl$_3$): 3.89(3H,s)
5.34(2H,s)
6.40(1H,s)
6.97–7.11(3H,m)
7.25–7.31(1H,m)
7.41–7.47(6H,m)
7.65(1H,s)
7.91(1H,bd).

By a similar procedure to Example I(2), the above compound was converted to its hydrochloride.

EXAMPLE 12

1-{3-(4-Ethoxyphenyl)-5-isoxazolyl}-3-(1-imidazolyl)methylindole hydrochloride

In 20 ml of DMF were dissolved 2.0 g (10 mmol) of 3-(1-imidazolyl)methylindole, followed by the addition of 0.45 g (11 mmol) of 60% sodium hydride. The resultant mixture was stirred at room temperature for 15 minutes. Added further at room temperature were 2.5 g (11 mmol) of 3-(4-ethoxyphenyl)-5-chloroisoxazole synthesized in a similar manner to the procedures of Referential Example 1. The resulting mixture was stirred, as it was, for 6 hours for reaction. The reaction mixture was transferred into 100 ml of ice water, followed by extraction with ethyl acetate. The resultant organic layer was washed with water and then dried over anhydrous magnesium sulfate. The solvent was distilled off, whereby the title compound was obtained as colorless crystals.

Yield: 1.8 g (46%)
Melting point: 182°–184° C.
NMR($\delta$ ppm, CDCl$_3$): 1.4(3H,t,J=12Hz)
4.1(2H,q,J=12Hz)
5.3(2H,s)
6.3(1H,s)
6.8–8.0(12H,m).

By a similar procedure to Example 1(2), the above compound was converted to its hydrochloride.

The molecular formulae, melting points and elemental analysis data of the salts of the compounds in Example 1 to Example 12 are summarized in Table 5.

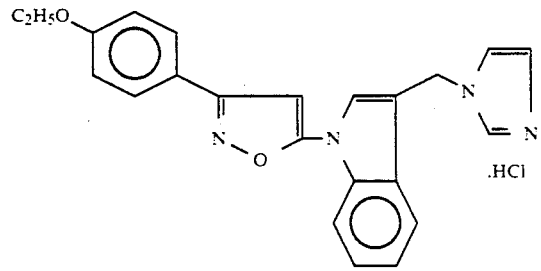

TABLE 5

| Ex. | R$_4$ | R$_2$ | Molecular formula | m.p. (°C.) | Elemental analysis data (%) Top: Calculated Bottom: Found | | | |
|---|---|---|---|---|---|---|---|---|
| | | | | | C | H | N | Cl |
| 1 | H | H | C$_{21}$H$_{16}$N$_4$O.HCl | 213–215 | 66.93 | 4.55 | 14.87 | 9.41 |
| | | | | | 66.21 | 4.47 | 14.59 | 9.08 |
| | | | | | C | H | N | Cl |
| 2 | H | CH$_3$ | C$_{22}$H$_{18}$N$_4$O.HCl | 208.5–210 | 67.59 | 4.91 | 14.34 | 9.07 |
| | | | | | 67.56 | 4.92 | 14.20 | 9.37 |
| | | | | | C | H | N | F | Cl |
| 3 | 4-F | H | C$_{21}$H$_{15}$FN$_4$O.HCl | 214–215 (Decomp'd) | 63.84 | 4.08 | 14.18 | 4.81 | 8.97 |
| | | | | | 63.43 | 3.93 | 14.17 | 4.31 | 8.88 |
| | | | | | C | H | N | Cl |
| 4 | 4-Cl | H | C$_{21}$H$_{15}$ClN$_4$O.HCl | 219–221 (Decomp'd) | 61.33 | 3.92 | 13.62 | 17.24 |
| | | | | | 60.97 | 3.71 | 13.63 | 16.71 |
| | | | | | C | H | N | Cl |
| 5 | 4-CH$_3$ | H | C$_{22}$H$_{18}$N$_4$O.HCl | 206–208 (Decomp'd) | 66.98 | 4.70 | 14.20 | 8.98 |
| | | | | | 66.79 | 4.81 | 14.03 | 8.68 |
| | | | | | C | H | N | Cl |

TABLE 5-continued

[Structure shown with R4 on phenyl, isoxazole ring, indole, imidazole-type ring with R2, ·HCl]

| Ex. | R4 | R2 | Molecular formula | m.p. (°C.) | Elemental analysis data (%) Top: Calculated Bottom: Found | | | |
|---|---|---|---|---|---|---|---|---|
| 6 | 4-OCH$_3$ | H | C$_{22}$H$_{18}$N$_4$O$_2$.HCl | 224–225 | 64.94 | 4.71 | 13.77 | 8.71 |
|   |   |   |   |   | 64.74 | 4.70 | 13.71 | 8.74 |
|   |   |   |   |   | C | H | N | Cl |
| 7 | 4-CN | H | C$_{22}$H$_{15}$N$_5$O.HCl.½H$_2$O | 242–244 (Decomp'd) | 64.31 | 3.93 | 17.05 | 8.63 |
|   |   |   |   |   | 64.98 | 3.95 | 17.07 | 8.57 |
|   |   |   |   |   | C | H | N | F | Cl |
| 8 | 4-CF$_3$ | H | C$_{22}$H$_{15}$F$_3$N$_4$O.HCl | 226–228 | 59.40 3.62 12.59 12.81 4.79 |
|   |   |   |   |   | 59.08 3.54 12.48 12.56 4.77 |
|   |   |   |   |   | C H N Cl |
| 9 | 2-Cl | H | C$_{21}$H$_{15}$ClN$_4$O.HCl | 192–194 | 61.33 | 3.92 | 13.62 | 17.24 |
|   |   |   |   |   | 61.30 | 4.04 | 13.59 | 17.09 |
|   |   |   |   |   | C | H | N | Cl |
| 10 | 3-Cl | H | C$_{21}$H$_{15}$ClN$_4$O.HCl | 228–229 | 61.33 | 3.92 | 13.62 | 17.24 |
|   |   |   |   |   | 61.41 | 3.97 | 13.71 | 17.03 |
|   |   |   |   |   | C | H | N | Cl |
| 11 | 3-OCH$_3$ | H | C$_{22}$H$_{18}$N$_4$O$_2$.HCl | 189–192 | 64.94 | 4.71 | 13.77 | 8.71 |
|   |   |   |   |   | 64.94 | 4.76 | 13.68 | 8.75 |
|   |   |   |   |   | C | H | N | Cl |
| 12 | 4-OCH$_2$CH$_3$ | H | C$_{23}$H$_{20}$N$_4$O$_2$.HCl | 228–230 | 65.63 | 5.03 | 13.31 | 8.42 |
|   |   |   |   |   | 65.92 | 5.02 | 13.25 | 8.37 |

EXAMPLE 13

1-{3-Phenyl-5-( 1,2,4-oxadiazolyl)}-3-(1-imidazolyl)-methylindole hydrochloride

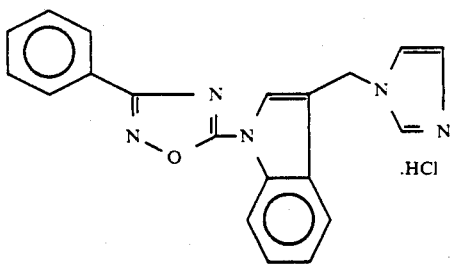

In 20 ml of dry DMF were dissolved 1.5 g (7.6 mmol) of 3-( 1-imidazolyl)methylindole, followed by the addition of 0.36 g (9 mmol) of 60% sodium hydride under ice cooling. The resultant mixture was stirred at room temperature for 5 minutes. Added further were 1.5 g (8.3 mmol) of 3-phenyl-5-chloro-1,2,4-oxadiazole synthesized in Referential Example 3. The resulting mixture was reacted at room temperature for 1.5 hours. After DMF was distilled off from the reaction mixture, ethyl acetate and water were added to the residue, followed by separation of the organic layer. The organic layer was dried and then purified by silica gel column chromatography (solvent: chloroform/methyl alcohol=50/1). The reaction product thus obtained was recrystallized from ethyl acetate, whereby the title compound was obtained as colorless crystals.

Yield: 2.16 g (83%)

Melting point: 161°–163° C.
NMR(δ ppm, CDCl$_3$): 5.36(2H,s)
7.04(1H,bs)
7.16( 1H,bs)
7.24–7.64(6H,m)
7.64–7.80(2H,bd)
8.08–8.30(2H,m)
8.44(1H,bd).

By a similar procedure to Example 1(2), the above compound was converted to its hydrochloride.

EXAMPLE 14

1-(4-Phenyl-2-thiazolyl)-3-( 1-imidazolyl)-methylindole hydrochloride

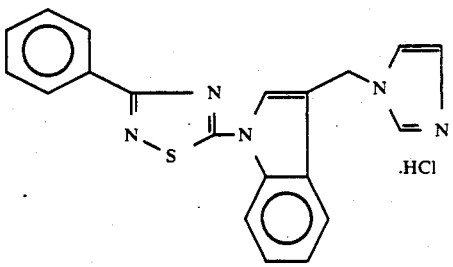

In 10 ml of dry DMF were dissolved 1.5 g (7.6 mmol) of 3-(1-imidazolyl)methylindole, followed by the addition of 0.35 g (8.8 mmol) of 60% sodium hydride under ice cooling. The resultant mixture was stirred at room temperature for 5 minutes Added further were 1.8 g (9.2 mmol) of 2-chloro-4-phenylthiazole synthesized in Referential Example 2. The resulting mixture was reacted at room temperature for 2 hours. After the solvent was distilled off from the reaction mixture, the residue was dissolved in ethyl acetate. The resultant solution was washed with water and then dried. Purification by silica gel column chromatography (solvent: chloroform/methyl alcohol=50/1) gave the title compound as colorless crystals.

Yield: 1.64 g (60%)

Melting point: 102°-105° C.

NMR(δ ppm, CDCl$_3$): 5.34(2H,s)

6.90-7.80( 11H,m)

7.94-8.10(2H,m)

8.38-8.54( 1H,bd).

By a similar procedure to Example 1(2), the above compound was converted to its hydrochloride.

EXAMPLE 15

1-(2-Benzoxazolyl)-3-(1-imidazolyl)methylindole hydrochloride

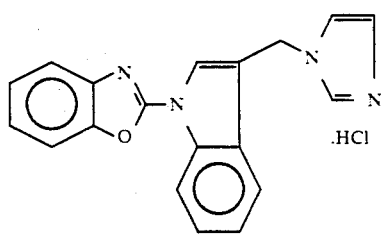

In 10 ml of dry DMF were dissolved 1.5 g (7.6 mmol) of 3-(1-imidazolyl)methylindole, followed by the addition of 0.35 g (8.8 mmol) of 60% sodium hydride under ice cooling. The resultant mixture was stirred at room temperature for 5 minutes. Further, a solution of 1.5 g (9.8 mmol) of 2-chlorobenzoxazole in 5 ml of dry DMF was added dropwise for reaction. The resulting mixture was stirred and reacted at room temperature for additional 20 minutes. The reaction mixture was then transferred into 200 ml of ice water, and crude crystals so formed were collected by filtration. The crude crystals were dissolved in chloroform, and the solution was washed with water. The organic layer was dried and the solvent was distilled off. The residue was recrystallized from a mixed solvent of ethyl acetate and hexane, whereby the title compound was obtained as colorless crystals.

Yield: 2.2 g (92%)

Melting point: 173°-175° C.

NMR(δ ppm, CDCl$_3$): 5.38(2H,s)

7.04-7.90(12H,m)

8.54-8.70( 1H,bd).

By a similar procedure to Example 1(2), the above compound was converted to its hydrochloride.

EXAMPLE 16

1-(2-Benzothiazolyl)-3-(1-imidazolyl)methylindole hydrochloride

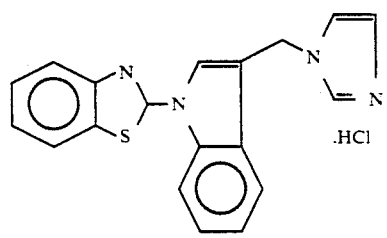

In 10 ml of dry DMF were dissolved 1.5 g (7.6 mmol) of 3-(1-imidazolyl)methylindole, followed by the addition of 0.35 g (8.8 mmol) of 60% sodium hydride under ice cooling. The resultant mixture was stirred at room temperature for 10 minutes. Further, a solution of 1.42 g (8.4 mmol) of 2-chlorobenzothiazole in 5 ml of dry DMF was added dropwise. The resulting mixture was stirred and reacted at room temperature for 1 hour. The reaction mixture was then added to 200 ml of ice water, and crude crystals so formed were collected by filtration. The crude crystals were washed with water and then dissolved in chloroform. After the resultant solution was washed with water and then dried, the solvent was distilled off. The residue was recrystallized from a mixed solvent of ethyl acetate and ethyl ether, whereby the title compound was obtained as colorless crystals.

Yield: 2.0 g (79%)

Melting point: 141°-143° C.

NMR(δ ppm, CDCl$_3$): 5.32(2H,s)

6.94-8.00(12H,m)

8.44-8.60(1H,bd).

By a similar procedure to Example 1(2), the above compound was converted to its hydrochloride.

The molecular formulae, melting points and elemental analysis data of the salts of the compounds in Example 13 to Example 16 are summarized in Table 6.

TABLE 6

(structure shown: R₁—N indole with CH₂—N imidazole·HCl)

| Ex. | R₁ | Molecular formula | m.p. (°C.) | Elemental analysis data (%) Top: Calculated Bottom: Found | | | | |
|---|---|---|---|---|---|---|---|---|
| | | | | C | H | N | S | Cl |
| 13 | (phenyl-substituted oxadiazole) | $C_{20}H_{15}N_5O \cdot HCl \cdot \tfrac{1}{4}H_2O$ | ≧230 | 62.83 / 62.67 | 4.35 / 3.86 | 18.32 / 18.11 | | 9.27 / 9.46 |
| 14 | (phenyl-substituted thiazole) | $C_{21}H_{16}N_4S \cdot HCl$ | 244–247 | 64.20 / 64.11 | 4.36 / 4.29 | 14.26 / 14.20 | 8.16 / 8.13 | 9.02 / 9.41 |
| 15 | (benzoxazole) | $C_{19}H_{14}N_4O \cdot HCl$ | ≧260 | 65.05 / 64.92 | 4.31 / 3.95 | 15.97 / 15.84 | | 10.11 / 9.86 |
| 16 | (benzothiazole) | $C_{19}H_{14}N_4S \cdot HCl$ | 249–251 | 62.20 / 64.29 | 4.12 / 3.93 | 15.27 / 15.23 | 8.74 / 8.58 | 9.66 / 9.90 |

We claim:

1. An imidazole derivative represented by the formula:

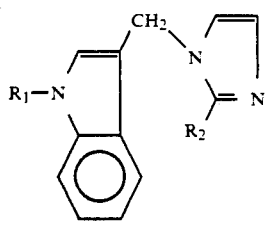

where R₁ is

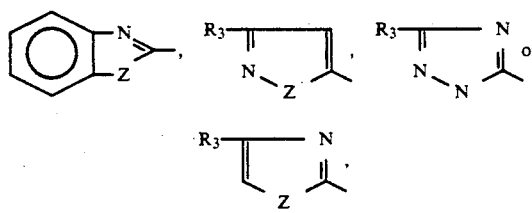

R₃ is a phenyl group or phenyl group substituted by at least one substituent selected from the group consisting of halogen atoms and lower alkyl, lower alkoxy, trifluoromethyl and cyano groups and Z being a sulfur or oxygen atom, and R₂ denotes a hydrogen atom or a lower alkyl group or a pharmaceutically acceptable salt thereof.

2. An antiepileptic composition comprising, together with a pharmaceutically acceptable carrier, as an effective ingredient an imidazole derivative of the formula:

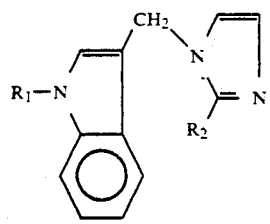

where R₁ is (same substituent structures as above)

R₃ is a phenyl group or phenyl group substituted by at least one substituent selected from the group consisting of halogen atoms and lower alkyl, lower alkoxy, trifluoromethyl and cyano groups, Z is a sulfur or oxygen atom, and R₂ denotes a hydrogen atom or a lower alkyl group or a physiologically-acceptable salt thereof.

* * * * *